(12) United States Patent
Ryan et al.

(10) Patent No.: US 6,281,509 B1
(45) Date of Patent: Aug. 28, 2001

(54) METHOD AND APPARATUS FOR IMAGING THROUGH 3-DIMENSIONAL TRACKING OF PROTONS

(75) Inventors: James M. Ryan, Lee; John R. Macri, Durham; Mark L. McConnell, Newmarket, all of NH (US)

(73) Assignee: University of New Hampshire, Durham, NH (US)

( * ) Notice: Subject to any disclaimer, the term of this patent is extended or adjusted under 35 U.S.C. 154(b) by 0 days.

(21) Appl. No.: 09/476,702

(22) Filed: Jan. 3, 2000

Related U.S. Application Data

(60) Provisional application No. 60/114,614, filed on Jan. 4, 1999.

(51) Int. Cl.[7] ............................................. H01J 37/244
(52) U.S. Cl. ............................................ 250/397; 250/367
(58) Field of Search ................................. 250/306, 397, 250/367

(56) References Cited

U.S. PATENT DOCUMENTS

| | | | | |
|---|---|---|---|---|
| 5,103,098 | * | 4/1992 | Fenyves | 250/367 |
| 5,374,824 | * | 12/1994 | Chaney et al. | 250/367 |
| 5,714,761 | * | 2/1998 | Fay | 250/367 |
| 5,905,263 | * | 5/1999 | Nishizawa et al. | 250/367 |
| 6,008,496 | * | 12/1999 | Winefordner et al. | 250/397 |

* cited by examiner

*Primary Examiner*—Bruce C. Anderson
(74) *Attorney, Agent, or Firm*—Devine, Millimet & Branch, P.A.; Paul C. Remus; Todd A. Sullivan

(57) ABSTRACT

A method and apparatus for creating density images of an object through the 3-dimensional tracking of protons that have passed through the object are provided. More specifically, the 3-dimensional tracking of the protons is accomplished by gathering and analyzing images of the ionization tracks of the protons in a closely packed stack of scintillating fibers.

9 Claims, 8 Drawing Sheets

METHOD AND APPARATUS FOR IMAGING THROUGH 3-DIMENSIONAL TRACKING OF PROTONS

STATEMENT OF RELATED CASES

This application claims the benefit of U.S. Provisional Application No. 60/114,614, filed Jan. 4, 1999.

This invention was made with government support under NASA contract/grant No. NAGW-5076 awarded by the National Aeronautics and Space Administration. The government has certain rights in the invention.

BACKGROUND OF THE INVENTION

High energy proton irradiation is a recent development in the treatment of cancer and other diseases. A high-energy proton beam is used to deliver radiation as precisely as possible to a tumor volume, minimizing radiation delivery to healthy tissue.

One of the challenges in so using a proton beam is the precise positioning of the patient (and tumor). It has been suggested that the proton beam itself can be used to position the tumor, both before and during treatment. Romero, J. L., et al., 1995 Nucl. Instr. Meth., A 356, 558. If a high energy proton beam is used, such that the protons are not stopped inside the patient, the protons can be used to generate a density image of the patient. Romero, et al., suggested generating such an image through the use of wire chambers to determine proton location and layers of plastic scintillators monitored by photomultiplier tubes to determine proton energy. This method assumes, however, that a proton's energy is absorbed in part in the patient but that its direction remains unchanged. In fact, protons are scattered and often exit the patient in a direction different from the incident direction, thereby degrading the image quality. If it is possible to determine a proton's direction after exiting the patient, scattered protons can be identified and discarded. Other protons that are also included in radiation "background" can also be identified and discarded. The present invention allows the precise tracking, i.e. the determination of the location, energy and direction, of a proton.

The present invention is a method and apparatus for imaging objects. It does so by the 3-dimensional tracking of protons that have passed through the object to be imaged. The tracking is accomplished by gathering and analyzing images of the ionization tracks of the protons in a closely packed stack of scintillating fibers. The fibers are arranged in stacked layers with the fibers in a given layer orthogonal to those in the layers immediately adjacent.

A similar arrangement of scintillating fibers has been used to determine the location of the incidence of ionizing radiation. No suggestion was made, however, for its use in determining the direction or energy of the ionizing radiation. Fenyves U.S. Pat. No. 5,103,098.

A similar arrangement of scintillating fibers has also been proposed for measuring solar neutrons in the 20–200 MeV range. Measurements of the solar neutrons are proposed by imaging the ionization tracks of protons produced as a result of the elastic scattering of the solar neutrons off hydrogen within the scintillating fibers. Ryan, et al., 1997 SPIE, Vol. 3114, 514. No suggestion was made, however, for its use in any type of imaging of objects through which protons have passed, the protons being tracked having been produced within the scintillating fibers of the detector.

The present invention can be used to generate density images of patients for diagnosis and treatment. It can also be used to generate density images of other objects. It can also be used, for example, to measure the thickness at various points of objects of uniform composition.

The present invention has significant advantages as opposed to existing systems of imaging using protons. As noted above, it precisely tracks the protons, determining the direction, as well as the location and energy, of each proton that has passed through the object to be imaged. This capability allows the effective identification and substraction of radiation background, permitting a higher signal to noise ratio and higher contrast images. The present invention also permits real-time imaging.

SUMMARY OF THE INVENTION

The object of the present invention is to provide a new method and apparatus for imaging an object through the 3-dimensional tracking of protons that have passed through the object. A further object of the present invention is to accomplish the 3-dimensional tracking of the protons by gathering and analyzing images of the ionization tracks of the protons in a closely packed stack of scintillating-fibers.

The present invention comprises a plurality of scintillating fibers arranged in a stack; a system for gathering the images of proton ionization tracks in the scintillating fibers; and a system for analyzing the images of the proton ionization tracks to create an image of the object.

The scintillating fibers in a preferred embodiment are arranged in a stack comprising a plurality of stacked layers with the fibers in a given layer positioned lengthwise and substantially parallel to each other. Each layer is one fiber diameter in depth and substantially parallel to each adjacent layer. The fibers in a given layer are positioned orthogonally to those in immediately adjacent layers.

The system for gathering the images of proton ionization tracks in the scintillating fiber stack comprises an energy measuring system, a recording system, and a processing system. One end of each fiber in the stack is coupled to the energy measuring system, and the other end of each fiber is coupled to the recording system. In a preferred embodiment, the energy measuring system comprises one or more photomultiplier tubes, and the recording system comprises one or more chains of fiber-optic tapers, first and second image intensifiers, and charge-coupled device ("CCD") cameras.

When one of the protons strikes a scintillating fiber, it produces photons within the fiber by the scintillation process. Photons are collected and processed at both ends of the fiber. The energy measuring system collects photons from one end of each of the fibers that has been struck. When the aggregate photons so collected indicate an energy deposited in the fiber stack within an established energy deposit window, the energy measuring system provides a signal to a trigger logic circuit. At the other end of each of the fibers that has been stuck, the recording system captures and holds photon images when the trigger logic circuit registers the proper coincidence.

The photon images are then fed into the processing system, which in a preferred embodiment comprises at least one digital processor and software, enabling storage and display of a form of the photon images. The form of the photon images may be either raw data or processed data. The processed data enables the analysis and display of an image of the ionization track, i.e. the location, energy and direction, of each incident proton that has passed through an object to be imaged.

The processed data is, in turn, fed into a system for analyzing the images of the proton ionization tracks. In a preferred embodiment, this system comprises at least one digital processor and software. This system analyzes the images of proton ionization tracks to create an image of the object.

IN THE DRAWINGS

DETAILED DESCRIPTION OF THE INVENTION

As is described in more detail below, the object of the present invention is to produce an image of an object through the 3-dimensional tracking of protons that have passed through the object. The present invention utilizes a plurality of scintillating fibers, constituting a scintillating fiber stack, to image ionization tracks of incident protons that have passed through the object. The images of the ionization tracks yield information about the protons, including their individual location, direction and energy, that can be used to produce an image of the object.

The present invention can be used to generate density images of patients for diagnosis and treatment. It can also be used to generate density images of other objects. It can also be used, for example, to measure the thickness at various points of objects of uniform composition.

Figure 1:
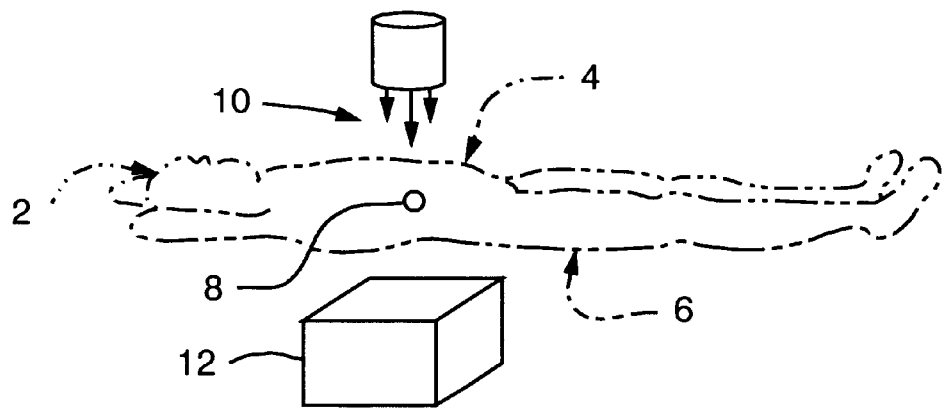
FIG. 1 is a perspective drawing of a system for proton imaging a patient according to an embodiment of the present invention.

By way of example, FIG. 1 illustrates a patient with a first side 4, a second side 6, and a tumor 8. It also depicts a beam of protons 10 directed at, and proximate, the first side 4 of the patient 2, and a plurality of scintillating fibers arranged in a stack 12, proximate the second side 6 of patient 2. The patient 2, the tumor 8, the beam of protons 10, and the scintillating fiber stack 12 are configured so that protons will pass through the patient and the tumor and strike the scintillating fiber stack.

More specifically, the present invention comprises a plurality of scintillating fibers arranged in a stack; a system for gathering images of proton ionization tracks in the scintillating fibers; and a system for analyzing the images of proton ionization tracks to create an image of an object.

Figure 2:
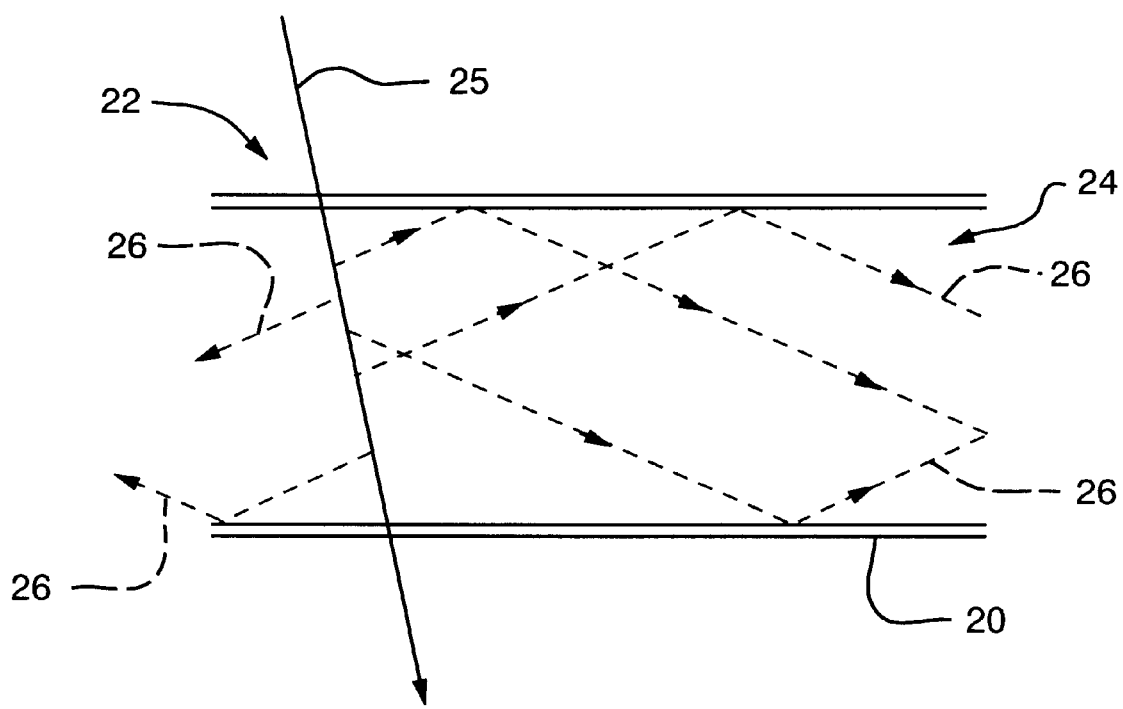
FIG. 2 illustrates a proton striking a scintillating fiber and producing photons therein in an embodiment of the present invention.

Referring to FIG. 2, a single scintillating fiber 20, with first end 22 and second end 24, is illustrated. Scintillating fibers are presently available from a number of commercial sources. A proton 25, enters, and may pass completely through, scintillating fiber 20. Photons 26 are produced within scintillating fiber 20 by the scintillation process. The attenuation length of the photons in the fibers is sufficient to allow photons to strike both ends of the fiber.

Figure 3:
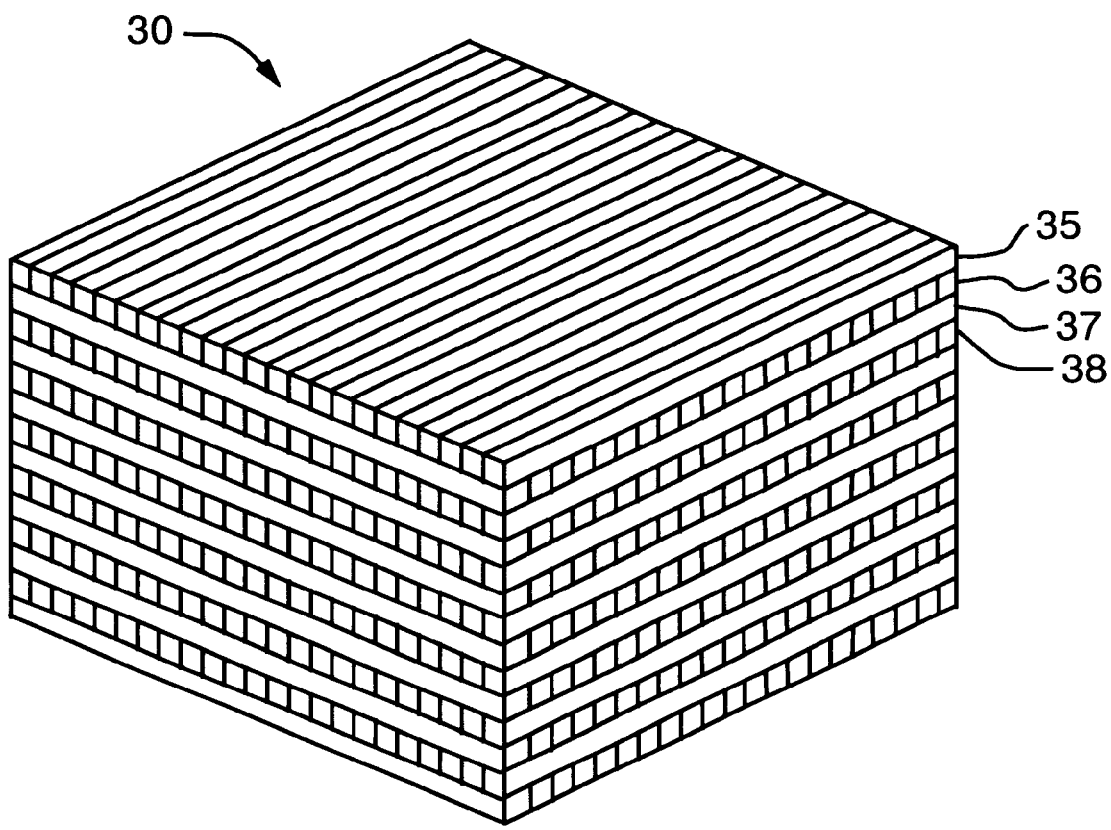
FIG. 3 is a perspective view of a scintillating fiber stack according to an embodiment of the present invention.

Referring to FIG. 3, a plurality of scintillating fibers arranged in a stack 30 is illustrated. Fiber layer 35 comprises lengths of scintillating fibers positioned lengthwise and substantially parallel to each other. Each layer of scintillating fibers preferably has a depth of the diameter of a single fiber and is substantially parallel to each other layer of scintillating fibers. Fiber layers 35, 36, 37, and 38 are produced in this manner. The scintillating fibers comprising layer 35 are positioned at a 90 degree angle to the fibers of layer 36. Additional layers are preferably added to the stack as shown in FIG. 3 wherein each layer has its respective fibers positioned at a 90 degree angle to the fibers of each adjacent layer.

Figure 4:
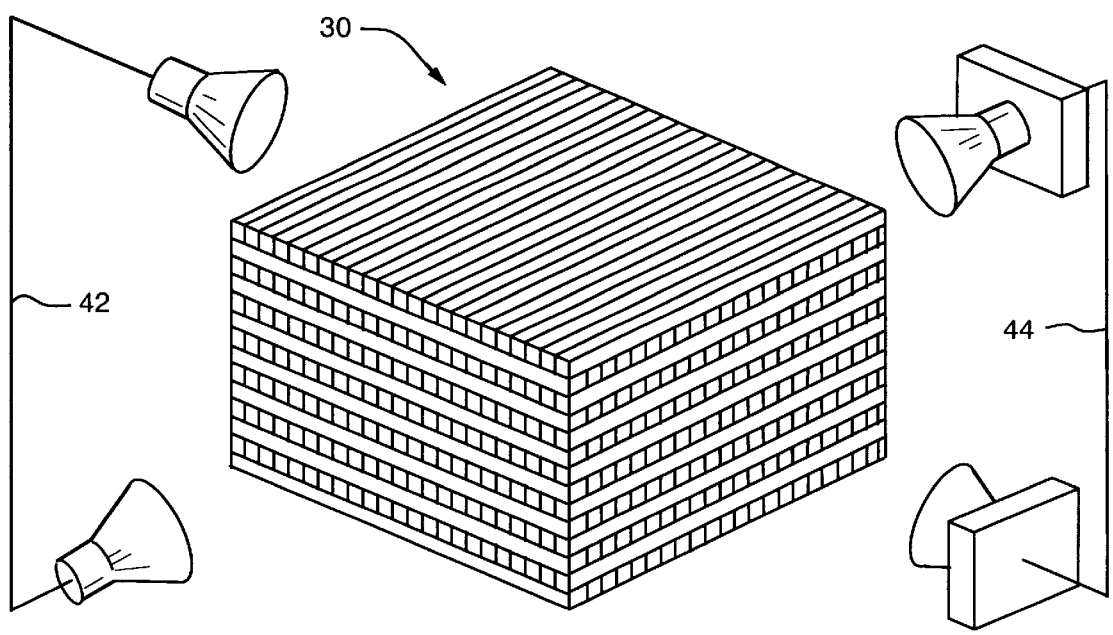
FIG. 4 is a perspective view of a scintillating fiber stack, an energy measuring system, and a recording system according to an embodiment of the present invention.

The present invention also comprises a means for gathering the images of proton ionization tracks in the scintillating fiber stack. In a preferred embodiment, the image gathering means comprise a system for gathering the images of proton ionization tracks in the scintillating fiber stack further comprising an energy measurement system, a recording system, and a processing system. Referring to FIG. 4, a perspective view of the scintillating fiber block 30, the energy measuring system 42, and the recording system 44 is illustrated. The first end of each fiber in the stack is connected to the energy measuring system 42. The second end of each fiber in the stack is connected to the recording system 44. In a preferred embodiment, the energy measuring system comprises one or more photomultiplier tubes available from a number of commercial sources. Also in a preferred embodiment, the recording system comprises one or more chains of fiber-optic tapers, first and second image intensifiers, and charge-coupled device ("CCD") cameras. A recording system in a preferred embodiment is illustrated in FIG. 5, showing an imaging chain consisting of a fiber optic taper 46, a first image intensifier 48, a second image intensifier 50 and a CCD camera 52.

Fiber optic tapers reduce image size. Image intensifiers convert incoming photons to electrons, much like photomultipliers, and then use one or more microchannel plates to increase the number of electrons by factors of 1000 or more. These electrons then interact with a phosphor screen, reverting to (visible) light. The image produced on the phosphor screen is visible for an amount of time that depends on the type of phosphor selected. Fiber optic tapers and image intensifiers are commercially available.

Figure 5:
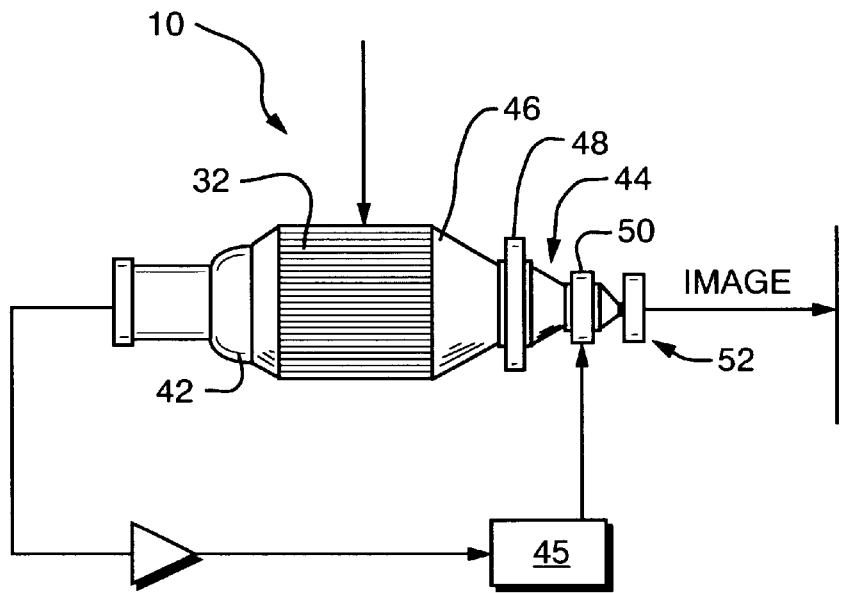
FIG. 5 is a functional diagram of a scintillating fiber stack, an energy measuring system, and a recording system according to an embodiment of the present invention.

Referring to FIG. 5, when a proton 10 strikes a scintillating fiber in the stack 30, it produces photons within the fiber by the scintillation process. The energy measuring system 42, which in this embodiment comprises a photomultiplier tube, collects photons from one end of the scintillating fibers that have been struck by a proton. The photomultiplier tube provides a pulse height that is a measure of the total energy deposited in the fiber block by one proton. When the aggregate photons indicate an energy deposited in the fiber block within an established energy deposit window, the photomultiplier tube provides a signal to the trigger logic circuit 45. At the other end of each of the fibers struck by a proton, the recording system 44, which in this embodiment comprises an imaging chain of a fiber optic taper 46, a first image intensifier 48, and a second image intensifier 50 and a CCD camera 52, demagnifies, captures and holds the photon images.

The first image intensifier 46 is always gated "ON." Its phosphor holds a photon image for approximately 1 ms, long enough for the trigger logic circuit to validate an event. The second image intensifier 50 is normally gated "OFF," and no photon image is passed to the CCD camera. However, when the trigger logic circuit 45 registers the proper coincidence, the second image intensifier is gated "ON" and outputs a further intensified image to the CCD camera, and the photon image is gathered. Without the first image intensifier 48, the scintillating photons would vanish by the time the trigger logic circuit gated an intensifier and a CCD camera.

Alternative optoelectronic devices can be employed in the energy measuring system, in place of a photomultiplier tube, or in the recording system, in place of elements in the imaging chain described above. Alternative optoelectronic devices that serve both the energy measurement and image recording functions can also be employed. Arrays of avalanche photodiodes, multi-anode photomultipliers, multi-pixel hybrid photodiodes, and electron bombardment CCD cameras are candidates for this application. With such devices, optoelectronic components need only be used on one end of the fiber.

Figure 6:
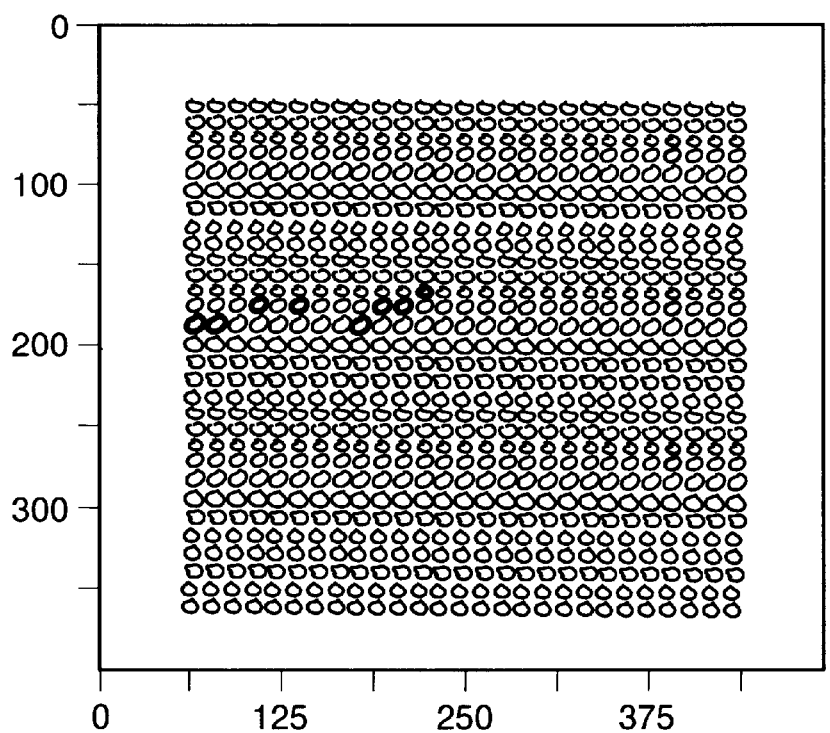
FIG. 6 illustrates the track of a 23 MeV proton in an embodiment of the present invention.

The photon images are then fed into the processing system, which in a preferred embodiment comprises at least one digital processor and certain additional hardware and software, enabling storage and display of a form of the photon images. The form of the photon images may be either raw data or processed data. The processed data enables the analysis of display of an image of the ionization track, i.e. the location, energy and direction, of each incident proton that has passed through an object to be imaged. FIG. 6 illustrates the track of a 23 MeV proton incident from the left on an embodiment of the present invention.

Figure 7A:
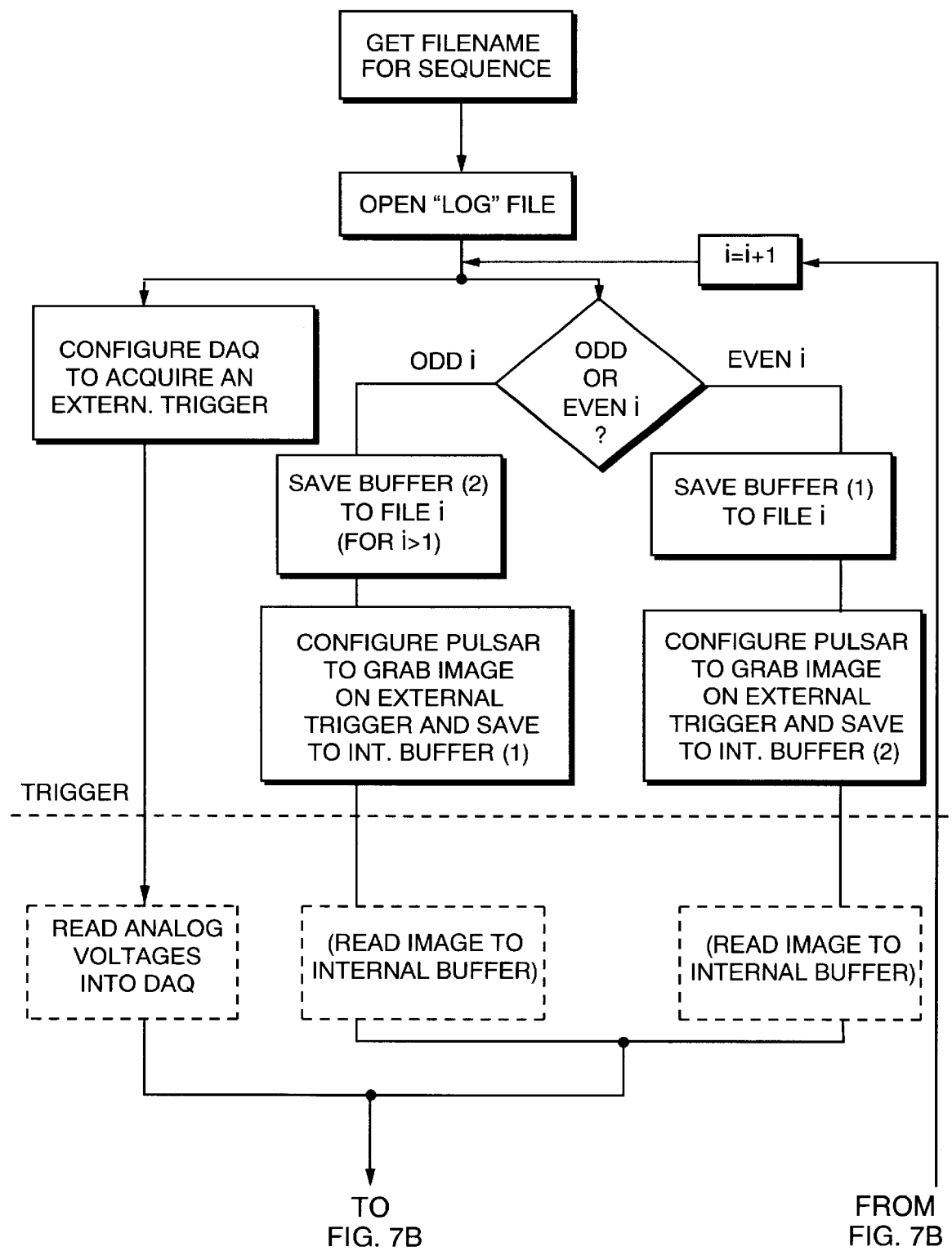
FIG. 7 is a flow chart of the software for the "Sequence" function according to an embodiment of the present invention.
Figure 7B:
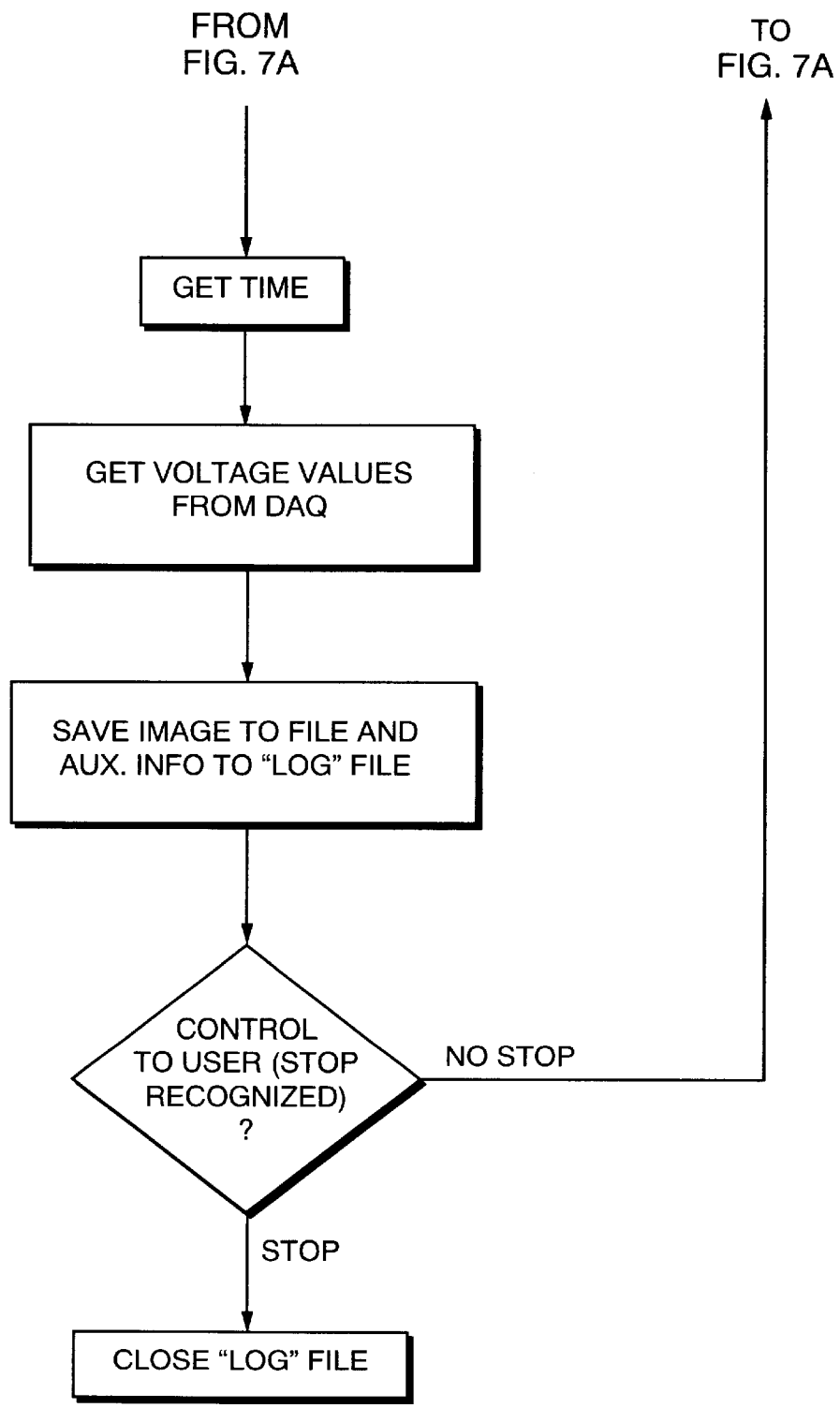

Aside from several monitoring and demonstration features, the additional hardware and software of the processing system has two main functions relevant to the actual measurements discussed: "Sequence" and "Mask." The software uses libraries from commercial sources for image manipulation and analysis including in a preferred embodiment, camera control functions for a PULSAR frame grabber board; camera control functions for a data acquisition ("DAQ") board; and a user-friendly interface. The main program, the "Sequence" function, automatically acquires and saves a series of images while generating a "log" text file listing the individual image file names, the time of image capture, and the voltage corresponding to the photomultiplier pulse height for each image. FIG. 7 illustrates a flow chart for a preferred embodiment of the "Sequence" function program, in which the dashed squares represent functions executed by the PULSAR and DAQ boards in response to an external trigger.

After opening a text "log" file and writing certain preliminary information, the program configures first the DAQ board and then the PULSAR board for externally triggered data acquisition. Prompted by an external trigger, supplied directly to both the DAQ board and the PULSAR board, the DAQ board performs the analog-to-digital conversion of the voltages inputs, while the PULSAR board acquires a CCD image and stores it in an internal buffer. Then the system clock time is recorded. The DAQ voltage values and the system time are written to the "log" file. At this point, the user can exit the loop by toggling the sequence switch in the menu. Otherwise, the program continues by configuring the DAQ board for a new acquisition and saving the last acquired buffer into an image file identified by the number "i."

The two parallel image-saving loops increase the maximum camera frame rate the program can handle. While the contents of one image buffer are being written to file, the second buffer can already be filled with the next image. The program pauses and waits for the next trigger at the "save buffer to file" points; this command is not executed until after the "read image to internal buffer" for the same buffer is executed.

Figure 8:
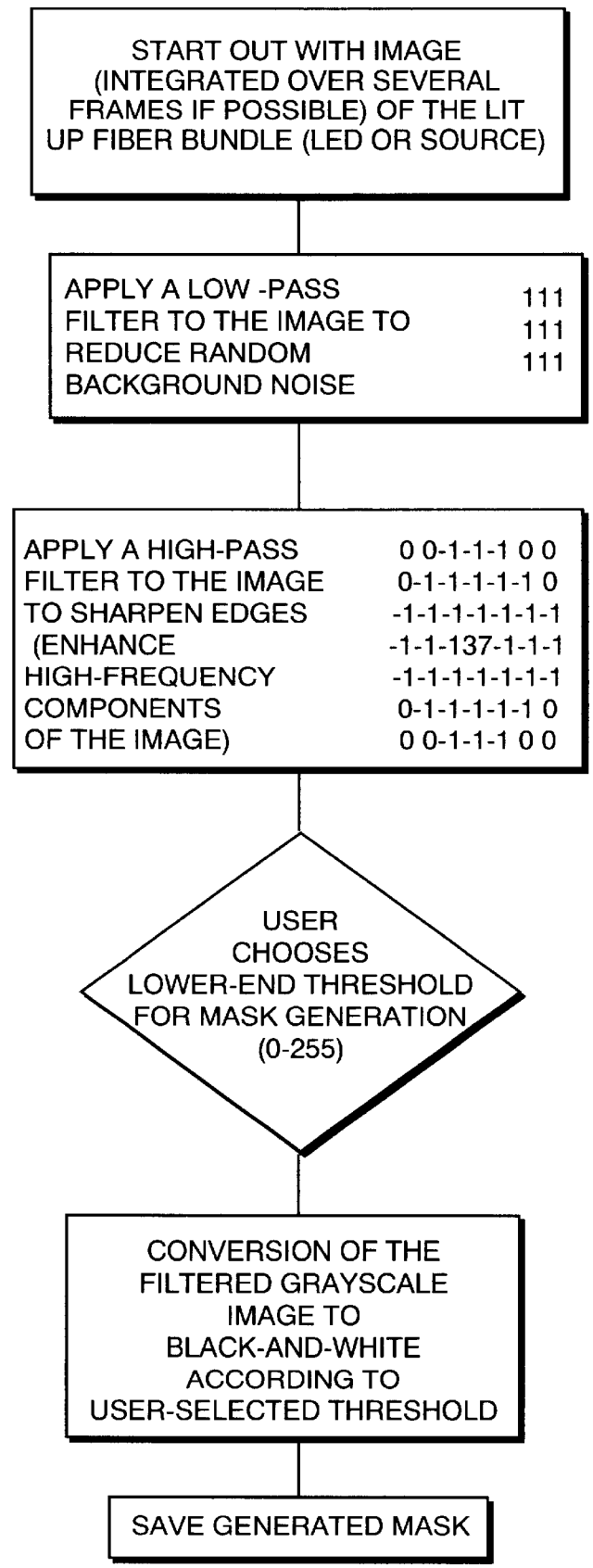
FIG. 8 is a flow chart of the software for the "Mask" function according to an embodiment of the present invention.
Figure 9:
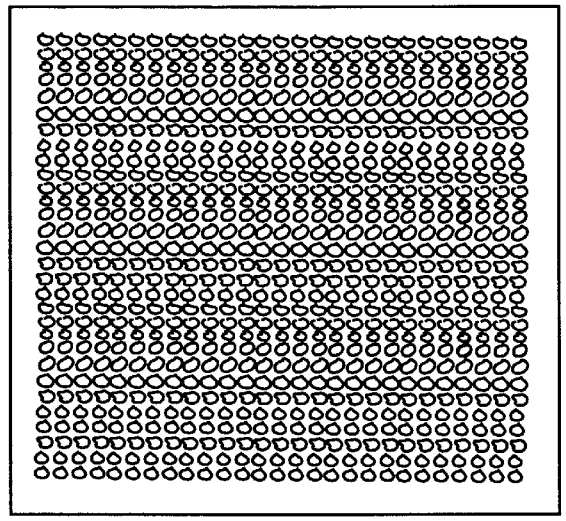
FIG. 9 illustrates an image of a mask according to an embodiment of the present invention.

The program for the "Mask" function allows the creation of a black-and-white mask of all fibers from an image of illuminated fibers. This mask is used in reconstructing the proton track image relative to fiber boundaries rather than individual CCD pixels. The initial image for mask generation can be obtained by exposing the bundle to a strong gamma-ray source. FIG. 8 illustrates a flow chart for a preferred embodiment of the "Mask" function program, and FIG. 9 illustrates an image of such a mask.

In processing mask data, a low-pass filter is first applied to the image. Each pixel is replaced by the average of the 3×3 pixel square surrounding it. A high-pass filter with a matrix of approximately the same size as a single fiber is then applied to the image. By subtracting the result of a low-pass-filtering (the average of the surrounding area) from the initial image (which would, in the matrix image, correspond to just the number one in the central pixel, with all others set to zero), one obtains the high-frequency component of the image. Selecting the high-frequency component of an image emphasizes the edges of features. Clearly defined fiber boundaries are necessary for a useful "Mask" image. Finally, a user-specified threshold is applied to the image, converting the filtered grayscale image to the final black-and-white mask.

The processed data from the processing system is, in turn, fed into a means for analyzing the images of the proton ionization tracks. In a preferred embodiment, the image analyzing means comprises a system for analyzing the images of the proton ionization tracks further comprising at least one digital processor, and certain additional hardware and software known to persons skilled in the art, including Monte Carlo simulation software. This system analyzes the images of the proton ionization tracks. It first eliminates those tracks that do not meet criteria established for creating a high contrast image of the object to be imaged. For example, in one embodiment of the present invention, this system eliminates those tracks that deviate more than a specified angle from the direction of the incident protons, indicating protons that have been scattered in the object to be imaged. It also eliminates those tracks that start within the fiber stack, indicating recoil protons resulting from neutron collisions with hydrogen atoms within the fiber stack, and those tracks that traverse more than a specified number of layers within the fiber stack, indicating protons that have not passed through the object to be imaged or background protons of too high energies.

Figure 10:
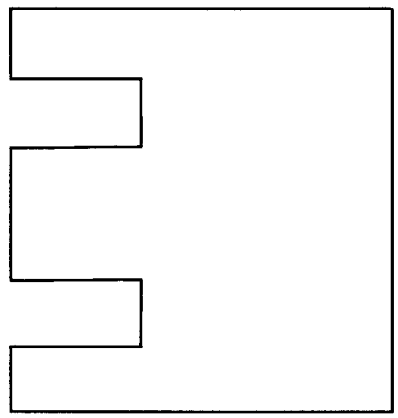
FIG. 10 illustrates an acrylic phantom to be imaged.
Figure 11:
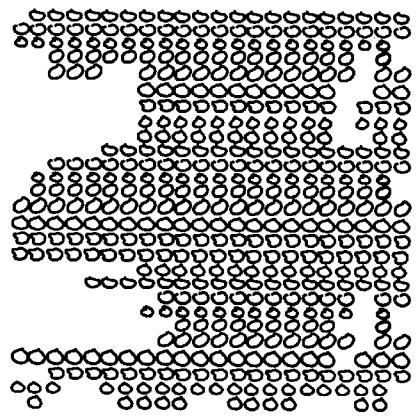
FIG. 11 illustrates an image of the object shown in FIG. 10 produced by 67.5 MeV protons that have traversed the object and struck an embodiment of the present invention.

This system then uses the remaining proton ionization tracks to create a density image of the object through which the protons passed. By measuring the lengths of these proton ionization tracks, i.e. the number of layers of the fiber stack through which the protons pass, it can determine the energy of the protons. The protons of relatively lower energy have lost relatively more energy by passing through a relatively denser portion of the object. The protons of relatively higher energy have lost relatively less energy by passing through a relatively less dense portion of the object. FIG. 10 illustrates an acrylic phantom to be imaged by a preferred embodiment of the present invention, and FIG. 11 illustrates an image of the object in FIG. 10 produced by 67.5 MeV protons that have passed through the object and struck a preferred embodiment of the present invention.

The invention has been particularly shown and described above with reference to various preferred embodiments, implementations and applications. The invention is not limited, however, to the embodiments, implementations or applications described above, and additions thereto may be made within the scope of the invention.

What is claimed:

1. A method for imaging through 3-dimensional tracking of protons, comprising:

a) configuring a plurality of scintillating fibers in a stack comprising a plurality of layers, each layer (i) comprising a plurality of scintillating fibers positioned lengthwise substantially parallel and immediate each adjacent scintillating fiber within the same layer, (ii) being one scintillating fiber diameter in depth and being positioned parallel each adjacent layer, and (iii) being further positioned so that the scintillating fibers in each layer are orthogonal to the scintillating fibers in each adjacent layer;

b) configuring an object to be imaged between and proximate a source of protons directed at the object and the scintillating fiber stack, thereby allowing the protons to pass through the object and strike the scintillating fiber stack, leaving ionization tracks in the scintillating fiber stack;

c) gathering images of the proton ionization tracks in the scintillating fiber stack, including measuring the energy of the portons producing the porton ionization tracks;

d) analyzing the images of the proton ionization tracks to create an image of the object.

2. The method of claim 1 wherein the object comprises a patient to be diagnosed or treated.

3. The method of claim 1 wherein the object exhibits uniform composition by varying thickness in the direction of the protons.

4. An apparatus for imaging through 3-dimensional tracking of protons, comprising:

a) a plurality of scintillating fibers, each with two ends, in a stack comprising a plurality of layers, each layer (i) comprising a plurality of fibers positioned lengthwise substantially parallel and immediate each adjacent fiber within the same layer, (ii) being one fiber diameter in depth and being positioned parallel each adjacent layer, and (iii) being further positioned so that the fibers in each layer are orthogonal to the fibers in each adjacent layer;

b) configuring an object to be imaged between and proximate a source of protons directed at the object and the scintillating fiber stack, thereby allowing the protons to pass through the object and strike the scintillating fiber stack, leaving ionization tracks in the scintillating fiber stack;

c) a means for gathering images of the proton ionization tracks in the scintillating fiber stack further comprising an energy measuring means coupled to an end of each scintillating fiber, a recording means coupled to an end of each scintillating fiber, and a processing means; and d) a means for analyzing the images of the proton ionization tracks to create an image of the object.

5. The apparatus of claim 4 wherein the object comprises a patient to be diagnosed or treated.

6. The apparatus of claim 4 wherein the object exhibits uniform composition but varying thickness in the direction of the protons.

7. An apparatus for imaging through 3-dimensional tracking of protons, comprising:

a) a plurality of scintillating fibers, each with a first end and a second end, in a stack comprising a plurality of layers, each layer (i) comprising a plurality of scintillating fibers positioned lengthwise substantially parallel and immediate each adjacent scintillating fiber within the same layer, (ii) being one scintillating fiber diameter in depth and being positioned parallel each adjacent layer, and (iii) being further positioned so that the scintillating fibers in each layer are orthogonal to the scintillating fibers in each adjacent layer;

b) an object to be imaged between and proximate a source of protons directed at the object and the scintillating fiber stack, thereby allowing the protons to pass through the object and strike the scintillating fiber stack, leaving ionization tracks in the scintillating fiber stack;

c) a system for gathering images of the proton ionization tracks in the scintillating fiber stack, further comprising an energy measuring system coupled to the first end of each scintillating fiber, a recording system coupled to the second end of each scintillating fiber, and a processing system; and d) a system for analyzing the images of the proton ionization tracks to create an image of the object.

8. The apparatus of claim 7 wherein the energy measuring system comprises a photo multiplier tube.

9. The apparatus of claim 7 wherein the recording system comprises a chain, in turn further comprising a fiber-optic taper, an image intensifier, and a charge-coupled device camera.

* * * * *